US008105745B2

(12) United States Patent
Ho et al.

(10) Patent No.: US 8,105,745 B2
(45) Date of Patent: Jan. 31, 2012

(54) RADIATION CROSSLINKER

(75) Inventors: Peter Kian-Hoon Ho, Singapore (SG);
Lay-Lay Chua, Singapore (SG);
Siong-Hee Khong, Singapore (SG);
Sankaran Sivaramakrishnan, Singapore (SG); Perq-Jon Chia, Singapore (SG)

(73) Assignee: National University of Singapore, Singapore (SG)

( * ) Notice: Subject to any disclaimer, the term of this patent is extended or adjusted under 35 U.S.C. 154(b) by 826 days.

(21) Appl. No.: 11/994,565

(22) PCT Filed: Jul. 4, 2006

(86) PCT No.: PCT/SG2006/000186
§ 371 (c)(1),
(2), (4) Date: Jul. 21, 2008

(87) PCT Pub. No.: WO2007/004995
PCT Pub. Date: Jan. 11, 2007

(65) Prior Publication Data
US 2009/0004402 A1    Jan. 1, 2009

(30) Foreign Application Priority Data
Jul. 4, 2005  (CA) ........................... 2511354

(51) Int. Cl.
*G03F 7/012* (2006.01)
*C07C 247/18* (2006.01)
(52) U.S. Cl. ................. 430/197; 430/270.1; 552/8
(58) Field of Classification Search ........... 430/270.1, 430/197; 552/8
See application file for complete search history.

(56) References Cited

U.S. PATENT DOCUMENTS 5,962,192 A    10/1999  Holman, III et al.
6,252,096 B1 *  6/2001  Spielmann et al. ............... 552/8

FOREIGN PATENT DOCUMENTS

| WO | WO 98/22541 A2 | 5/1998 |
| WO | WO 98/22542 | 5/1998 |
| WO | WO 2004/100282 A2 | 11/2004 |

OTHER PUBLICATIONS

International Search Report dated Oct. 16, 2006 for International Application No. PCT/SG2006/000186.
STN File CA, Abstract 141:425105, & WO 2004/100282 A2, Chua et al., Nov. 18, 2004; 3 pages.
Yan, M. et al, "Bis(perfluorophenyl azides) as highly efficient crosslinking agents for poly(vinyl phenol)," Reactive & Functional Polymers, vol. 43, pp. 221-225, 2000.
STN File CA, Abstract 132:315733, Yan et al., Reactive & Functional Polymers, vol. 43, pp. 221-225, 2000; 1 page.
Yan, M. et al, "Evaluation of bis(perfluorophenyl azide)s as cross-linkers for a soluble polyimide," Journal of Materials Chemistry, 6(8), pp. 1249-1252, 1996.
STN File CA, Abstract 125:169305, Yan et al., Journal of Materials Chemistry, 6(8), pp. 1249-1252, 1996; 2 pages.
Cai et al, "Development of Highly Efficient Deep-UV and Electron Beam Mediated Cross-Linkers: Synthesis and Photolysis of Bis(perfluorophenyl) Azides," Chemistry of Materials, 6(10), pp. 1822-1829, 1994.
STN File CA, Abstract 121:217443, Cai et al., Chemistry of Materials, 6(10), pp. 1822-1829, 1994; 3 pages.
Cai et al, "Conducting Polymers as Deep-UV and Electron Beam Resists: Direct Production of Micrometer Scale Conducting Structures from Poly(3-octylthiophene)," Journal of Molecular Electronics, 7(2), pp. 63-68, 1991.
STN File CA, Abstract 116:22343, Cai et al., Journal of Molecular Electronics, 7(2), pp. 63-68, 1991; 2 pages.
Cai et al, "Diazo- and Azido-Functionalized Glutaraldehydes as Cross-Linking Reagents and Potential Fixatives for Electron Microscopy," Bioconjugate Chemistry, 2(1), pp. 38-43, 1991.
STN File CA, Abstract 114:117886, Bioconjugate Chemistry, 2(1), pp. 38-43, 1991; 5 pages.
STN File CA, Abstract 136:363794, & Picq et al., Journal of Medicinal Chemistry (2002), 45(8), 1678-1685; 2 pages.
STN File CA, Abstract 135:61147, & US 6252096 B1, Spielmann et al., Jun. 26, 2001; 2 pages.
STN File CA, Abstract 131:250464, & US 5962192 A, Holman et al., Oct. 5, 1999; 1 page.
STN File CA, Abstract 127:11138, & SU 1369546 A1, Kulygina et al., Jul. 20, 1996; 1 page.
STN File CA, Abstract 122:229271, & Pandurangi et al., Journal of the Chemical Society, Dalton Transactions: Inorganic Chemistry (1995), (4), 565-9; 1 page.
STN File CA, Abstract 112:76525, & Orlova et al., Izvestiya Sibirskogo Otdeleniya Akademii Nauk SSSR, Seriya Khimicheskikh Nauk (1989), (3), 117-24; 1 page.
STN File CA, Abstract 110:192356 & Kmihalina et al., Izvestiya Sibirskogo Otdeleniya Akademii Nauk SSSR, Seriya Khimicheskikh Nauk (1988), (3), 92-5; 2 pp.
STN File CA, Abstract 96:20048 & Orlova et al., Izvestiya Sibirskogo Otdeleniya Akademii Nauk SSSR, Seriya Khimicheskikh Nauk (1981), (4), 125-9; 1 page.
STN File CA, Abstract 90:120588, & Bolton et al., Journal of the Chemical Society, Perkin Transactions 2: Physical Organic Chemistry (1972-1999) (1978), (12), 1288-92; 1 page.
STN File CA, Abstract 85:20922 & Gerasimova et al., Zhurnal Organicheskoi Khimii (1976), 12(4), 856-8; 1 page. Touwslager et al., "I-Line lithography of poly(3,4-ethylenedioxythiphene) electrodes and application in all-polymer integrated circuits," Applied Physics Letters, vol. 81(24), 2002.

* cited by examiner

*Primary Examiner* — John Chu
(74) *Attorney, Agent, or Firm* — Beyer Law Group LLP

(57) ABSTRACT

There is provided a class of crosslinking compound, said compound comprising (i) one or more fluorinated aromatic group; and (ii) one or more ionizable group, wherein the crosslinking compound is soluble in at least one polar solvent. Methods of preparing the crosslinking compounds are also disclosed. There is further provided devices obtainable from the methods of preparing the crosslinking compounds.

18 Claims, 4 Drawing Sheets

RADIATION CROSSLINKER

BACKGROUND

A. Field of Invention

The present invention is in the fields of polymers and electronics, including organic electronics, plastic electronics, and organic semiconductor devices. In particular, it concerns a crosslinker, and a method of making a device using a crosslinker.

B. Background Information

Radiation- or thermal-induced crosslinking of insulating, semiconductive and conductive polymer films is a crucial enabling step in the fabrication of multilayered device components and integrated circuits (ICs). This allows for the repeated deposition or patterning of multilevels in the device and/or the IC. One way to achieve radiation crosslinking is through the use of radiation-sensitive crosslinkers. Although such materials have been commercially available for a long time, most of them are not generally applicable to organic polymer semiconductor device technologies because of the severe restrictions on purity. The crosslinking has to be performed without causing degradation of the electrical performance of the device. This often requires the stringent exclusion of electrical traps, from the crosslinked products or by-products, and for applications in light-emitting diodes, also of states that could interact with and degrade the luminescence efficiency of the semiconductive material. A number of radiation crosslinking systems have been recently disclosed using oxetane reactions, epoxy reactions, cinnamate dimerisation reactions.

The crosslinking of water-soluble conductive polymer systems using bis(phenyl azide) crosslinkers have been proposed for the interconnects and electrodes in organic semiconductor device technologies [F. J. Touwslager, N. P. Willard and D. M. de Leeuw, "I-line lithography of poly(3,4-ethylenedioxythiophene) electrodes and application in all-polymer integrated circuits", Applied Physics Letters, 81 (2002) pp. 4556-4558]. In the cited literature, a high concentration of the crosslinker is required, typically in excess of 10 w/w %. This suggests that the crosslinking efficiency is relatively low, and there is a high concentration of by-products generated. This is probably suitable for a range of applications that are not sensitive to these by-products.

In view of the above, there is a need to obtain improved crosslinkers, preferably with high efficiency and minimum concentration of by-products generated. Further, it is a preferable aim of the present invention to provide single and/or multilayer structures in organic electronic devices obtained from the crosslinkers. Another preferably aim of the present invention is to provide a new method for making the devices.

SUMMARY OF THE PRESENT INVENTION

In a first aspect a new class of crosslinkers is provided.

The general formula of this class of crosslinking compound is given by formula (1):

(1)

wherein $Ar_FZ$ comprises one or more fluorinated aromatic group;

and R comprises one or more ionisable group, wherein the crosslinking compound is soluble in at least one polar solvent.

In one embodiment, the polar solvent is selected from the group of consisting of water, methanol, ethanol, propanol, dimethylsulfoxide, N,N-dimethylformamide, N,N-dimethylacetamide, N-methylpyrrolidone.

In still another embodiment the one or more fluorinated aromatic group may comprise two fluorinated aromatics. In another embodiment the crosslinking compound may comprise a linker connecting the two fluorinated aromatics. In yet another embodiment each of the one or more fluorinated aromatic group may be independently selected from the group consisting of fluorinated phenyl and fluorinated napthyl. In still another embodiment each of the one or more fluorinated aromatics may be selected from an alike one, or a same one, of the group consisting of fluorinated phenyl and fluorinated napthyl. In yet another embodiment each of the one or more fluorinated aromatics bears fluorine atoms ortho in position to an azide group. In another embodiment the two fluorinated aromatics may be fluorinated phenyl.

In yet another embodiment the ionisable group may be selected from the group consisting of an acid group, a cationic group, a basic group and an anionic group. In still another embodiment the acid group may be selected from the group consisting of a sulfonic acid, a phosphonic acid, a carboxylic acid. In yet another embodiment, the cationic group may be selected from the group consisting of a quaternary ammonium group and a pyridinium group. In yet another embodiment the basic group may be selected from the group comprising of amine. In another embodiment, the anionic group may be selected from the group consisting of a sulfonate, a phosphonate and a carboxylate.

In another embodiment the linker may be joined to each of the two fluorinated aromatics by an electron-withdrawing group. In yet another embodiment the electron-withdrawing group may be selected from the group consisting of a carbonyl, an ester and an amide. In still another embodiment the linker may be selected from the group consisting of a $C_1$ to $C_8$ alkylene, a cycloalkylene, and an alkylidene. In yet another embodiment the ionisable group may be bonded to the linker.

In another embodiment the linker comprises a bridge and the bridge may be selected from the group consisting of an alkylene, a carbonyl and an ethyleneglycol. In still another embodiment an absorption band may occur between 250 nm to 450 nm.

In one example of the first aspect, the crosslinking compound is of formula (2):

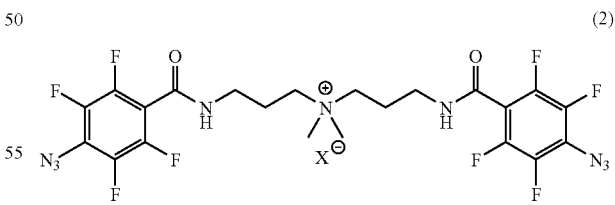

(2)

wherein X is selected from the group consisting of I, $PF_6$, $BF_4$, $ClO_4$ and $CF_3COO$.

In a third aspect a mixture comprising a polymer and the crosslinking compound according to the first aspect, wherein the concentration of the crosslinking compound is in the range of 0.1% to 20% w/w of the polymer is provided. In one form the concentration of the crosslinking compound may be in the range of 0.1% to 5.0%. In another form the polymer may be selected from the group consisting of polymers soluble in at least one polar solvents. In one embodiment, the polar solvent is selected from the group of consisting of water, methanol, ethanol, propanol, dimethylsulfoxide, N,N-dimethylformamide, N,N-dimethylacetamide, N-methylpyrrolidone. In yet another embodiment, the polymer is selected from the group consisting of poly(styrene sulfonic acid), poly(styrene sulfonate salt), poly(diallydimethylammonium salt), poly(ally amine), poly(3,4-ethylenedioxythiophene)-poly(styrene sulfonic acid), poly(3,4-ethylenedioxythiophene)-poly(styrene sulfonate salt).

In a fourth aspect a method of crosslinking a polymer, the method including the steps of (i) adding the crosslinking compound of the first aspect to the polymer of the third aspect in a polar solvent to give a solution; and (ii) depositing a film from the solution on a substrate; and (iii) soft-baking a film at temperature between 100° C. and 130° C.; and (iv) photo-crosslinking the film to form an insoluble crosslinked polymer.

In a fifth aspect a method of forming a device comprising a polymer is provided, the method including the steps of: (i) depositing a film from a solution comprising a polymer and the crosslinking compound of the first aspect on a substrate; and (ii) soft-baking the film at a temperature between 100° C. to 130° C.; and (iii) blanket photocrosslinking the film in step (ii) to form an insoluble crosslinked polymer.

In one form of the fifth aspect step (ii) may comprise soft-baking under flowing an inert atmosphere with moisture and oxygen of less than 100 ppm.

In another form of the fifth aspect step (iii) may comprise exposing the solution in step (ii) to radiation having a wavelength in a range of 250 nm to 450 nm in an inert atmosphere.

In a sixth aspect a method of forming a device, the method including the steps of: (i) depositing a film from a solution comprising a polymer and the crosslinking compound according to the first aspect on a substrate; (ii) soft-baking the film at a temperature between 100° C. to 130° C.; and (iii) photoexposing the film deposited in step (ii) through a patterned mask to form an insoluble crosslinked polymer; and (iv) developing the polymer in step (iii), is provided.

In one form of the sixth aspect step (ii) may comprise soft-baking in an inert atmosphere with moisture and oxygen of less than 100 ppm.

In another form of the sixth aspect step (iii) may comprise exposing through a photomask to a Deep UV (DUV) radiation having a wavelength between 250 nm and 450 nm in an inert atmosphere.

In a seventh aspect a new device structure for polymer semiconducting device comprising at least a layer obtained by the method in the fifth aspect or the sixth aspect is provided. In one embodiment, the device is an organic semiconducting device. In yet another embodiment, the device is an organic chemical sensor and actuator. In still another embodiment, the layer is a low-workfunction conducting polymer.

In an eight aspect use of the polymer semiconducting device obtained by the method of the fifth aspect or the sixth aspect.

BRIEF DESCRIPTION OF THE DRAWINGS

The present invention will be described in further detail with reference to the accompanying figures in which.

DETAILED DESCRIPTION OF THE INVENTION

Figure 1:
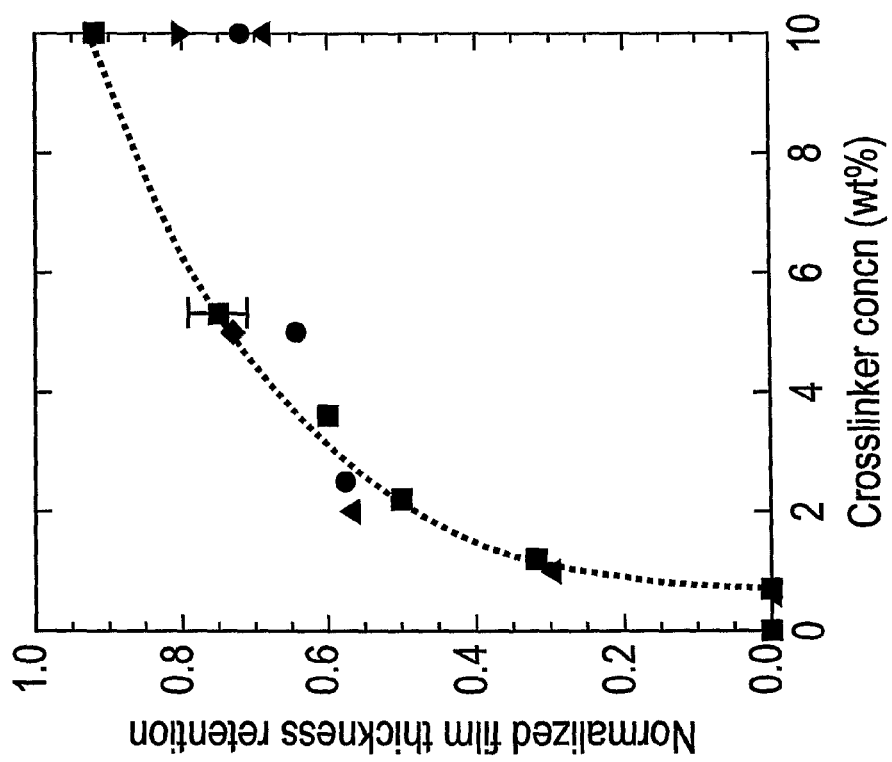
FIG. 1 Normalized film thickness retention for (squares) PSSH ($M_w$=530 k) with I deposited from MeOH solution (dotted line as visual guide), photoexposed and developed with $H_2O$; (diamond) PSSH with V, $H_2O$, developed with $H_2O$; (upright triangles) PSSNa ($M_w$=70 k) with V, $H_2O$, developed with MeOH; (inverted triangle) PDAMC1 ($M_w$=400 k) with V, $H_2O$, developed 3:1 i-PrOH—$H_2O$; (circles) PEDT:PSSTMA conducting polyelectrolyte complex with V, $H_2O$, developed with $H_2O$. Starting film thickness was between 50-200 nm. Film thickness was measured by profilometry or ellipsometry, before and after development. Typically films with the appropriate concentration of the crosslinker were spin-cast onto clean pristine or APS-treated Si wafers, dehydrated at 100° C. for 5 min (PSSH and PEDT:PSSTMA) or more strongly at 130° C. for 20 min (PSSNa and PDAMC1) in the glovebox, exposed to 254-nm DUV (ca. 1 mW cm$^{-2}$, 3-5 min) in nitrogen, and developed accordingly. A typical error bar is indicated.

The present invention relates, at least in part, to a fluorinated aromatic azide (FAA) crosslinker. In one form the fluorinated aromatic azide is a soluble bis (fluorinated aromatic azide) (herein after refer to as a bis (FAA)) based on the quaternization of N-methyl-N,N-dipropylene bis(4-azido-2,3,5,6-tetrafluorobenzamide) for crosslinking polyelectrolyte films.

In the context of the present invention it will be appreciated that a fluorinated aromatic azide may include a phenyl and biaryl moieties. A particular non-limiting example of a biaryl moiety is napthyl.

The fluorinated aromatic azide may have a fluorine atom at each position on the aromatic apart from the position at which the linker is attached. The fluorinated aromatic may have one, two, three, four, five or six or more fluorines. The azide group shall not occupy a position adjacent to the position where the linker is attached and shall be adjacent to fluorine atoms on each of its side. A person skilled in the art is readily able to select the number of fluorines depending on the aromatic.

In one embodiment the ionic or ionisable group may be directly linked and/or bonded to the aromatic.

Polyelectrolyte materials are characterized by the presence of charged groups in their repeats units, leading to solubility in water and alcohol solvents. They exhibit a high (reversible) moisture absorption and are particularly challenging to crosslink owing to the presence of this residual $H_2O$ and also to the negatively-charged and often highly-nucleophilic anions. Nevertheless it is still possible to crosslink under proper dehydrated conditions a wide range of polyelectrolytes using bis FAAs with higher efficiency than possible with prior art bis(aromatic azide)s. This ability to generally crosslink polyelectrolyte films opens new applications of these materials in sensor, separation and device fields.

The general formula of this class of crosslinking compound is given by formula (1):

(1)

where $Ar_FZ$ denotes one or more fluorinated aromatic group and R comprises one or more an ionisable group. The crosslinking compound is soluble in at least one polar solvents selected from the group of consisting of water, methanol, ethanol, propanol, dimethylsulfoxide, N,N-dimethylformamide, N,N-dimethylacetamide, N-methylpyrrolidone.

The crosslinking compound has one or more fluorinated aromatic group comprising two fluorinated aromatics and a linker which connects the two fluorinated aromatics. Each of the one or more fluorinated aromatics group is independently selected from the group consisting of fluorinated phenyl and fluorinated napthyl. In addition, each of the one or more fluorinated aromatics bears fluorine atoms ortho in position to an azide group. Preferably, the two fluorinated aromatics are fluorinated phenyl.

The ionisable group is selected from the group consisting of an acid group (e.g. a sulfonic acid, a phosphonic acid, a carboxylic acid), a cationic group (e.g. a quaternary ammonium group and a pyridinium group), a basic group (e.g. amine) and an anionic group (e.g. a sulfonate, a phosphonate and a carboxylate).

The linker may be joined to each of the two fluorinated aromatics by an electron-withdrawing group, which is selected from the group consisting of a carbonyl, an ester and an amide. The linker may also be selected from the group consisting of a $C_1$ to $C_8$ alkylene, a cycloalkylene, and an alkylidene. The ionisable group may be bonded to the linker.

The linker may comprise a bridge and the bridge may be selected from the group consisting of an alkylene, a carbonyl and an ethyleneglycol. Depending on the general formula, the crosslinking compound shows a significant absorption band between 250 nm to 450 nm.

There is provided a crosslinking compound of general formula (1) having the following formula (2):

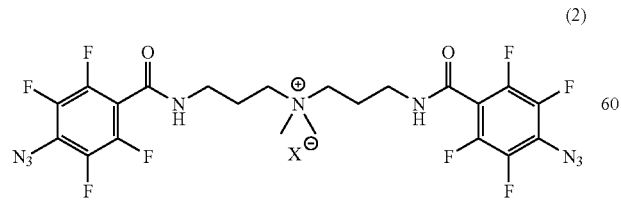
(2)

wherein X is selected from the group consisting of I, $PF_6$, $BF_4$, $ClO_4$ and $CF_3COO$.

Based on the formula (2), examples of suitable compounds includes:

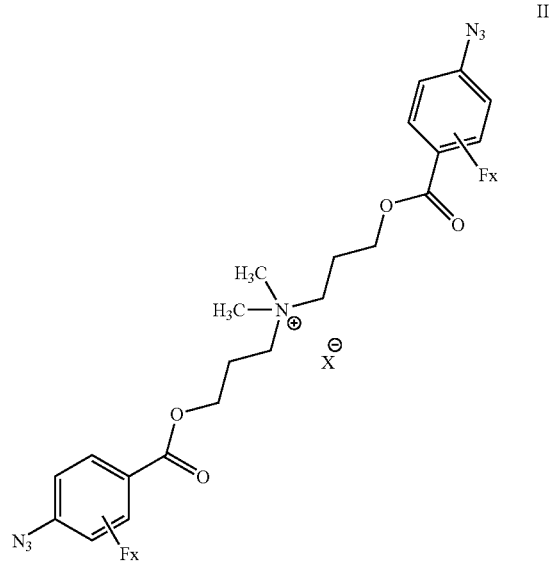
II where $X^-$ is an anion, e.g., $Cl^-$, $ClO_4^-$, $BF_4^-$, $PF_6^-$, $SbF_6^-$, $CF_3COO^-$, $CH_3C_6H_4SO_3^-$

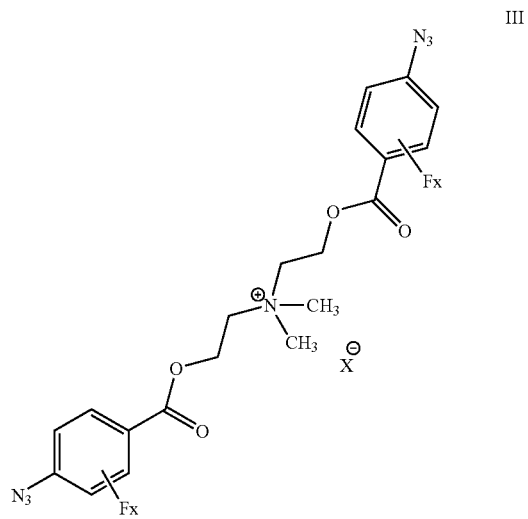
III where $X^-$ is an anion, e.g., $Cl^-$, $ClO_4^-$, $BF_4^-$, $PF_6^-$, $SbF_6^-$, $CF_3COO^-$, $CH_3C_6H_4SO_3^-$, $C_6H_4SO_3^-$

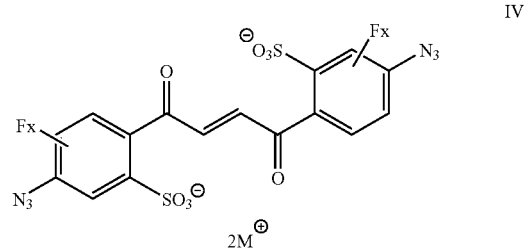
IV where M⁺ is a cation, e.g. H⁺, (CH₃)₄N⁺

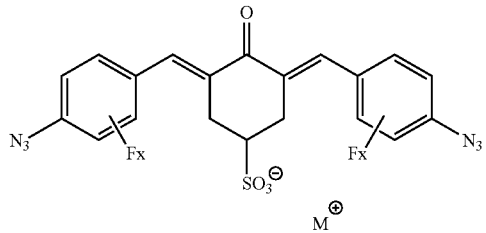

V where M⁺ is a cation, e.g. H⁺, (CH₃)₄N⁺

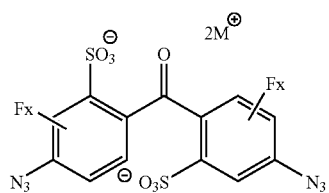

VI where M⁺ is a cation, e.g. H⁺, (CH₃)₄N⁺

In particular, compounds that bear an extended conjugation system in the bridging unit that joins the aromatic rings in the segment body $Ar_FZ$, such as IV and V above, have their electronic absorption band that shifted towards longer wavelengths in the UV and blue parts of the spectrum (300-450 nm) instead of the deep-UV (250-300 nm) that is required to photoexpose I-III. An extended conjugation system refers to one with alternating single and double bonds attached to the ring. Therefore the photocrosslinking can be activated using light of correspondingly longer wavelengths. This can be advantageous in certain cases to match to available high-power light sources, and in other cases to avoid the region of strong polymer matrix absorptions if any.

From this selection of compounds to illustrate the general principles, it is obvious that other variations and permutations of the bridging unit and water-solubilizing groups are possible to a person skilled in the art.

Examples of suitable polymers are polymers that are soluble in water and/or other polar solvents, including the lower alcohols (e.g. MeOH, EtOH, i-PrOH), DMF, DMAc, NMP and DMSO. The polymer is selected for its desired properties, examples or which are given below. Usually the polymer is a polyelectrolyte. A polyelectrolyte is one which bears ionic charges (cationic or anionic) or ionisable groups on its backbone usually at a concentration higher than 10% of the repeat units. The polymer can also be a non-polyelectrolyte. Examples of non-polyelectrolytes that are soluble in water and other polar solvents, and can therefore be photocrosslinked by the present method, include poly(vinyl alcohol), poly(hydroxystyrene). The photocrosslinker is then selected to be compatible with the polymer in the same solvent. This usually means that they need to be soluble in the same solvent so that they can be blended together into a stable formulation, and further that precipitation does not occur.

Non-limiting examples of polyelectrolytes that may be used with the crosslinker of the invention are listed as follows:

poly(styrene sulfonic acid)

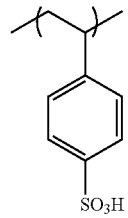

PI poly(styrene sulfonate, sodium salt)

PII poly(N,N,N,N-diallydimethylammonium chloride)

PIII

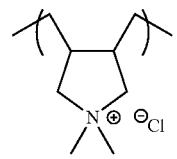

poly(N,N,N,N-diallydimethylammonium hexaflurophosphate)

PIV

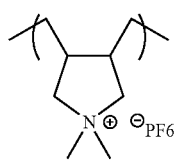

poly(3,4-ethylenedioxythiophene)-poly(styrene sulfonate, tetramethylammonium salt) polyelectrolyte complex

PV

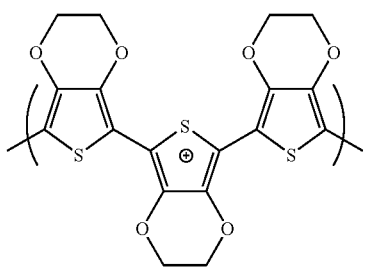

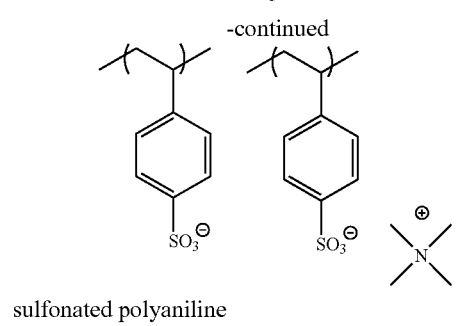

sulfonated polyaniline

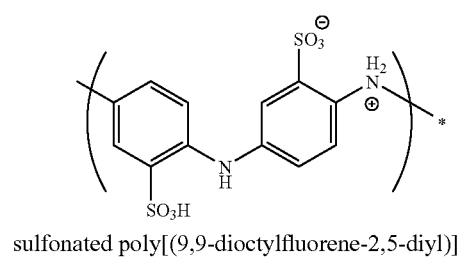

sulfonated poly[(9,9-dioctylfluorene-2,5-diyl)]

PVII sulfonated poly[(9,9-dioctylfluorene-2,5-diyl)-alt-phenylene-(N-phenyl)-iminophenylene]

PVIII

PVI

Polymers PI-IV are given here to illustrate the method can be used with non-conducting polyelectrolytes of both charge signs, i.e., both polycations and polyanions with different counterions including the acidic form (e.g. PI). These polymers are useful to fabricate insulating polymer layers, ion-sensing polymer and ion-actuating polymer layers. They can be used to fabricate ion-sensing layers because their counterions can be exchanged with other counterions of the same charge sign that are dissolved in the solution that is brought into contact with the polymer layer. As a result of this exchange, the properties of the polymer film changes (including optical and electrical), which leads directly to the sensing application. Also the volume and stress in the film changes, and this leads to mechanical deformation or bending of the substrate, which gives rise to actuating properties.

Polymers PV and PVI are given here to illustrate the method can also be used with electrically-conducting polyelectrolytes in the form of electrically-conducting interpolymer complexes (e.g. PV) and electrically-conducting polyions (e.g. PVI). Other variations are possible. These polymers are useful to fabricate conducting layers for interconnects as well as electrode applications by solution deposition. The ability to photocrosslink these materials efficiently then opens up the possibility to fabricate conductive polymer interconnects and electrodes by photolithography, as well as to fabricate robust polymer interconnects and electrodes that are mechanically stable and able to survive subsequent processing (since these structures after crosslinking are no longer soluble again).

Polymers PVII and PVIII are given here to illustrate the method can also be used with semiconducting polymers. In particular PVIII represents a member of a hole-transporting class of polymers based on the poly[fluorene-alt-triarylamine] motif; while PVII is a member of a class of light-emitting polymers (in this case a blue light-emitting polymer). Other variations are possible through selection of a different conjugation backbone from the general classes of fluorenes, thiophenes, phenylenes, and phenylenevinylenes, to obtain the desired pi-pi star gap, charge carrier mobility, refractive index, electron and hole transport levels, and other semiconducting and/or optoelectronic properties. The desired solubility in water and/or other polar solvents is generally achieved by incorporating ionic groups (which can be either cationic or anionic) or ionizable groups such as sulfonic acid groups (as indicated or these two polymers) or hydrogen-bonding groups. Such groups are selected on the basis of their compatibility with the desired semiconducting properties as well as their ability to produce the desired solubility characteristics. It is obvious that many variations are possible to a person skilled in the art.

The azide compounds according to the present invention are stable even in strongly acidic aqueous environment. To demonstrate this and their compatibility with strongly acidic polymers such as poly(styrenesulfonic acid), a major component of PEDT:PSS, I (16 mg mL$^{-1}$) is dissolved in acidified deuterated MeOD containing 2.4 M HCl and 6.5 M H$_2$O. Its $^{19}$F NMR spectrum is acquired within 5 min and again after 21 days. No observable change was found (ppm: 2,6-F, −68.2; 3,5-F, −76.9), indicating that the azide is stable in the acidic aqueous MeOD. This was further confirmed through FTIR analysis of the solid recovered by evaporation after the $^{19}$F NMR experiment. No change in the azide stretching intensity ($v_{as}N_3$, 2129 cm$^{-1}$) normalized against benzene ($v_{ring}$, 1546 cm$^{-1}$) was observed. Therefore these azides do not undergo any dark reactions with acid, water or alcohols at room temperature.

To assess the suitability of these azide compounds as deep UV (DUV) crosslinkers, the compounds are dissolved into various polyelectrolyte solutions at known weight ratios, spun as films onto clean pristine or APS-treated Si wafers, photoexposed through a mask if necessary to 254-nm DUV radiation from a low-pressure Hg lamp, and then the resultant image is developed with an appropriate solvent, usually H$_2$O or a lower alcohol or a mixture of the two. The DUV photoexposure was carried out in a glovebox (pO$_2$<10 ppm) to avoid photo-oxidation of the polymers. Before exposure, the film was pre-baked as appropriate (e.g. 100° C. for 5 min, or 130° C. for 20 min) in the glovebox to remove physisorbed H$_2$O which appears to interfere with the nitrene insertion reaction. The film retention was obtained by comparing the film thickness before and after development, using either spectroscopic ellipsometry or profilometry. Results are shown in FIG. 1. Without APS as adhesion layer, H$_2$O swells some of polyelectrolyte films sufficiently during development to lift films off from the substrate.

In this way, a poly(styrene sulfonic acid) (PSSH) film deposited from MeOH solution was successfully crosslinked with 1-10 wt % I upon DUV exposure. Microscopy shows a homogeneous film with no sign of phase separation (or crystallization) of the crosslinker. In the anhydrous state, PSSH is non-ionized but strongly acidic nevertheless. The developed film thickness increases with crosslinker concentration, reaching 0.92 (normalized to thickness before development) for 10 wt % of I. The exposure dose used (200 mJ cm$^{-2}$) was in excess of the 100-150 mJ cm$^{-2}$ required (which depends also on internal filter effect due to absorption of the polymer matrix at this wavelength) to ensure exhaustive reaction. Without the added crosslinker, PSSH requires >200 mJ cm$^{-2}$ to photo-crosslink, probably through a radical mechanism involving SO$_3$ loss based on infrared spectroscopy. Therefore the film retention measured here is solely due to the crosslinker. Similarly PSSH films deposited from H$_2$O solutions could also be crosslinked by DUV with V as photocrosslinker. The nitrene insertion crosslinking mechanism of bisPFAs therefore appears to be compatible even with strong poly acids.

Figure 2:
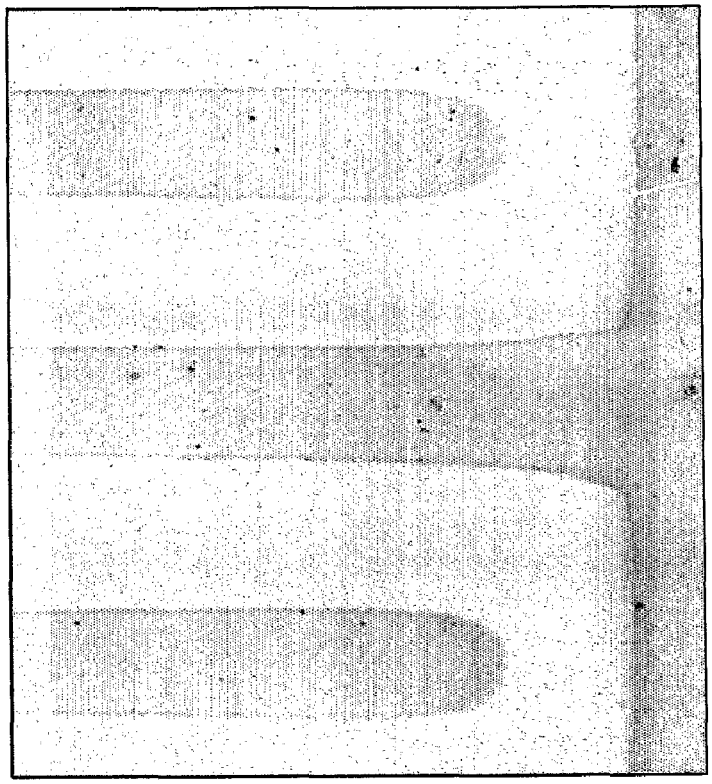
FIG. 2 Optical micrograph (500×500 μm) of shadow-mask photopatterned 60-nm-thick PEDT:PSSH conducting polymer thin film deposited initially from water-MeOH solution, exposed to 254-nm DUV through a shadow mask in nitrogen and developed with 1:1 vol i-PrOH-$H_2O$. Successful photo-induced crosslinking can be achieved for film thicknesses from few tens of nm to a few hundred nm.

To illustrate the generality of this bis (fluorinated phenyl azides) (bisFPA) approach, photocrosslinking a polyanion (poly(styrenesulfonate, sodium salt) (PSSNa, available from Sigma-Aldrich) and a polycation (polydiallydimethylammonium chloride) (PDAMCl, available from Sigma-Aldrich) film has been carried out. The data are plotted in FIG. 1. This shows that the bisFPAs are compatible also with the presence of nucleophilic anions (both sulfonate and chloride) in the polyelectrolyte. Both the electrically-conducting (and acidic) poly(3,4-ethylenedioxythiophene)-poly(styrene sulfonic acid) PEDT:PSSH polyelectrolyte complex and the electrically-conductive (but non-acidic) poly(3,4-ethylenedioxythiophene)-poly(styrene sulfonate tetramethylammonium) PEDT:PSSTMA complex are also crosslinked, both of these complexes are important water-soluble conducting-polymer systems. PEDT:PSSTMA was obtained from PEDT:PSSH by ion-exchange with tetramethylammonium bromide. This enables photo-patterning of conducting polymer systems as shown in FIG. 2. The electrical conductivity of PEDT:PSSTMA film before and after photo-crosslinking with these compounds are unchanged at 0.2 S cm$^{-1}$. Conductivity can be further enhanced by glycerol treatment.

The gel point is reached at typically <1 wt % of the crosslinker. Therefore the bisFPA methodology achieves considerably higher efficiency than with the unfluorinated bis (phenyl azide)s such as 4,4'-diazido-2,2'-stillbenedisulfonate disodium (available from Sigma-Aldrich), which requires more than 20 wt %. This is consistent with suppression of the parasitic nitrene ring expansion and intersystem crossing rates in the present crosslinkers.

The crosslinker concentration required to reach gel point is a function of the starting molecular weight of the polymer. Gelation occurs when an incipient fraction of polymer chains reaches infinite molecular weight (MW) at the critical crosslinking density, which leads to incipient insolubilization. Below the onset of gelation, no film is retained during development. Above gelation, the fraction of infinite-MW chains and thus the film retention upon development grows rapidly with crosslinking density. The critical crosslinking density $p_c$ is that at which the probability of forming the infinite chain becomes non-zero. This is given by $$\rho_c = \frac{1}{\overline{P}_w - 1}$$

where $\overline{P}_w$ is the mass-average degree of polymerization.

For the PSSNa film studied here, $\overline{P}_w$=380, which gives $p_c$=0.26 mol %, which theoretically requires 0.13 mol % of the bifunctional bisPFA crosslinker. The experimental gel point here occurs at ≈0.8 wt % which corresponds to 0.2 mol % of the crosslinker, indicating that the crosslinker is indeed relatively efficient. For the strongly acidic PSSH, the efficiency is evidently lower, since its M$_w$ corresponds to $\overline{P}_w$=2,900, which theoretically requires 0.03 mol % to reach gel point, compared to the experimental value of ≈0.2 mol %.

The exact concentration required to cross the gel point varies with the polymer and photocrosslinker. Therefore the suitable concentration range has to be determined for each desired polymer and photocrosslinker system. This can be done easily by measuring the fractional film retention after photoexposure as a function of concentration of the photocrosslinker in the film, as shown in FIG. 1. Usually, concentrations of 1-20 weight % of photocrosslinker to polymer should be sufficient. The preferred concentration is the concentration just beyond the gel point that gives at least 70% film retention. The film retention has to be taken into account in the design of the final film thickness. For example, if film retention is 70%, and one wishes to fabricate a final crosslinked film of thickness 70 nm, then the initial starting film thickness is given by 70 nm divided by 70% to be about 100 nm. However, it is possible to operate closer to the gel point (but obviously not below the gel point). Because film retention gets less as one approaches the gel point, the required initial film thickness to generate the desired final film thickness also gets progressively larger as one approaches the gel point.

This method enables photo-patterning of the polymer films. Line feature sizes down to 2 micrometers can be produced in films up to 300 nanometers thick.

The success of this FPA nitrene strategy appears to depend critically on the absence of residual $H_2O$ in the polymer films. Polyelectrolytes are unique in this respect because they equilibrate rapidly with humid air and can absorb huge quantities of $H_2O$. For both PSSNa and PDAMC1, which retain $H_2O$ more strongly, the required dehydration condition is harsher (130° C. for 20 min) than the milder conditions (100° C. for 5 min) appropriate for the other polyelectrolytes. From thermogravimetry, PSSNa and PDAMC1 are hydrated to ca. 3 and 3.5 $H_2O$/repeat unit respectively under ambient conditions (relative humidity 80%, 25° C.). It is estimated from the thermogravimetry curves that under the milder dehydration conditions employed here, there remains ca. 0.1-0.2 $H_2O$/repeat unit in PSSNa and PDAMC1, which appears already sufficient to quench the nitrene insertion mechanism. In contrast, although PSSH is even more hygroscopic in ambient (>6 $H_2O$/repeat unit), it does dehydrate rapidly in dry nitrogen, as evidenced by FTIR, and can thus be photocrosslinked successfully after the milder dehydration condition. Similarly, when the hydrophilic and hydrogen-bonding $Cl^-$ ion in PDAMC1 is exchanged with the far less hydrophilic $PF_6^-$ ion, the resultant weakly-hygroscopic $PDAMPF_6$ (0.7 $H_2O$/repeat unit at ambient, by thermogravimetry) can also be crosslinked under the milder dehydration condition. [$PDAMPF_6$ is confirmed by XPS (atomic stoichiometry: (found) $C_{8.0}N_{1.0}P_{1.0}F_{8.0}Cl_{0.0}$; (theory) $C_{8.0}N_{1.0}P_{1.0}F_{6.0}Cl_{0.0}$) and FTIR ($vPF_6^-$, 880 and 839 $cm^{-1}$). This material is soluble in DMF].

The level of $H_2O$ that can be tolerated must necessarily be related to the nature of the polyelectrolyte material itself and how mobile (or accessible) the $H_2O$ is. From these data, however, it appears that the level of water that can be tolerated is probably of the order of 0.3 $H_2O$/repeat unit or less.

Figure 3:
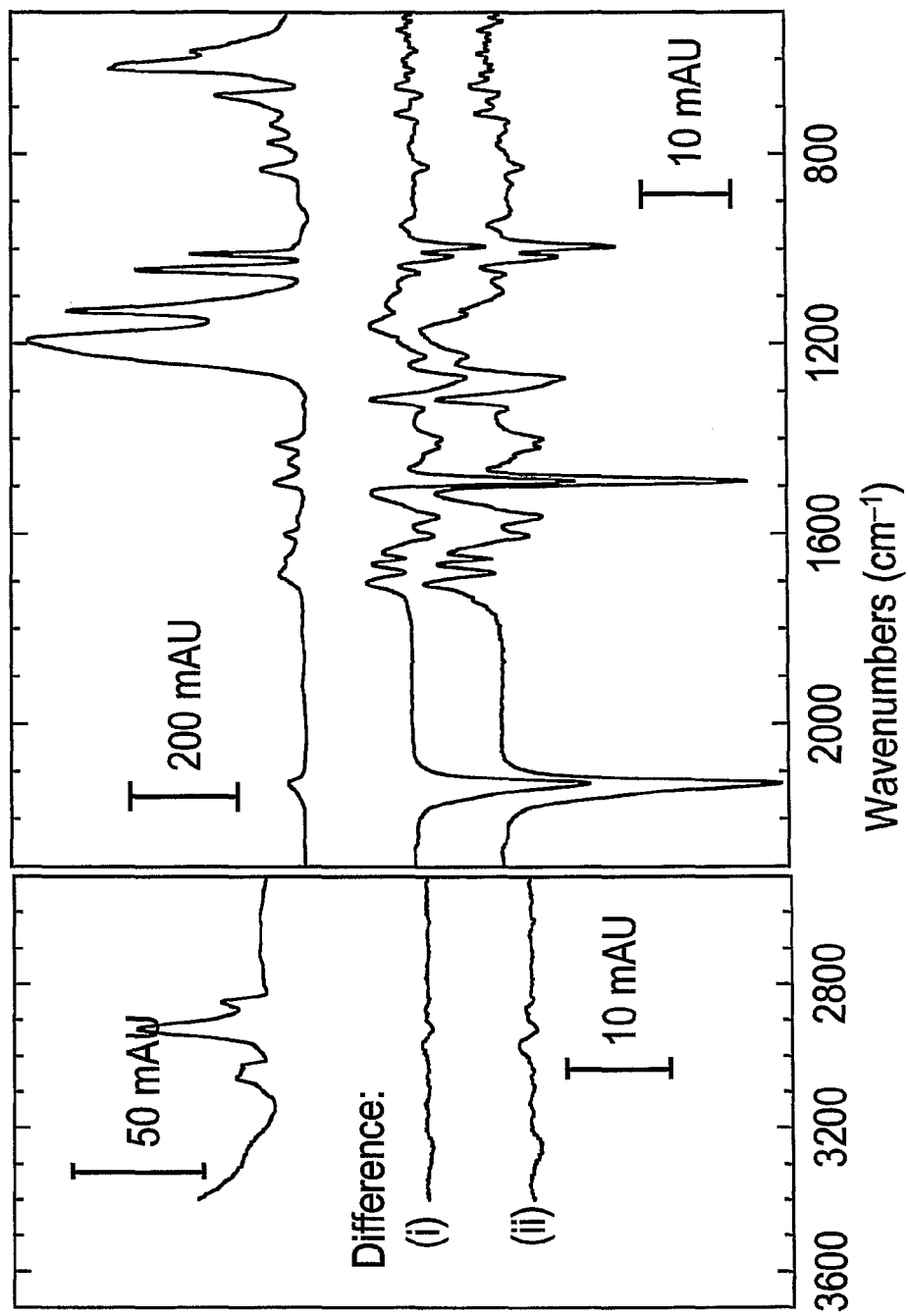
FIG. 3—log(Transmission) FTIR spectra of PSSNa thin film with 10 wt % V crosslinker on intrinsic Si wafer before (top spectrum) and after photoexposure (bottom two spectra). The spectra after photoexposure is presented as difference spectra with respect to the top spectrum: after (i) 30 mJ cm$^{-2}$ and (ii) 150 mJ cm$^{-2}$ exposure with 254-nm DUV. The data show a clear evolution of bands that identify the photo-reaction products. All FTIR spectra were acquired in a $N_2$-purged chamber.

To elucidate the impact of residual $H_2O$ on the fate of the photogenerated nitrenes, we tracked the FTIR spectra of a PSSNa film with 10 wt % V after dehydration at 100° C. 5 min in the glovebox, before exposure and upon 30 and 150 mJ $cm^{-2}$ of 254 nm DUV. The crosslinker concentration used in the film was thus 6 mol % based on azide units. Results are shown in FIG. 3. The expected progressive disappearance of the $N_3$ IR absorptions (2129, 1488, 1272 $cm^{-1}$) indicates that azide photolysis occurred smoothly to generate nitrenes. The aliphatic methylene vibrations ($v_{as}$=2926 and $v_s$=2844 $cm^{-1}$) and the ring stretching vibrations for p-disubstituted benzene rings (v=1604, 1569, 1411 $cm^{-1}$), decreased in intensity, while a new C—N (v=1316 $cm^{-1}$) band appeared and gained in intensity. These changes are consistent with the C—H insertion mechanism.

The loss in aliphatic CH intensity and p-substituted ring intensity were each ca. 2-3 mol % relative to the repeat unit. Loss of $SO_3^-$ is less than 1 mol %, and so electrophilic attack of the nitrene on $SO_3^-$ does not appear to be a critical side-reaction of these nitrenes. The growth of the broad band at 600-800 $cm^{-1}$ (assigned to $\omega_{NH2}$, in addition to the $\delta_{NH}$ at 715 $cm^{-1}$) suggests the formation of $NH_2$, a characteristic triplet-reaction product. This has not been observed in solid-state reactions of bisFPAs in organic-soluble polymer matrices. Its occurrence here suggests that intersystem crossing of the singlet nitrene to the triplet state does occur in these polyelectrolyte films. The triplet state then undergoes radical reactions, including H abstraction, which compete against crosslinking. The more rapid intersystem crossing is probably promoted through hydrogen-bonding with residual $H_2O$, analogous to the MeOH effect This also explains why the crosslinking yield tends to be low when the polyelectrolyte films are incompletely dehydrated, even at the level of mol % $H_2O$. In addition there is also evidence for formation of N=O as indicated by the growth of a peak at 1514 $cm^{-1}$, arising probably from OH trapping to the hydroxylamine followed by oxidation.

There is provided new devices in the field of organic polymer electronic devices and in sensors and actuators. The device is selected from the group consisting of organic light-emitting diodes, organic transistor, organic photovoltaic, organic memory device, organic chemical sensor, organic electrochemical sensor and organic actuator. The structures and their application are described in details as follows:

A. Low-Workfunction Polymer Electron-Injecting Film for p-i-n Trilayer Polymer Organic Light-Emitting Diode and Photodiodes A p-i-n trilayer polymer organic light-emitting diode (LED) comprises a hole-transporting electrically-conductive polymer layer (the p-layer) and an electron-transporting electrically-conductive polymer layer (n-layer) sandwiching the light-emitting polymer (LEP) layer (i-layer), wherein the n-layer is based on a conducting polymer, photocrosslinked, and preferably n-doped and surface-modified to give the desired low work-function required for electron injection. One or more of the electrically-conductive polymers is crosslinked.

Electrically-conductive polymer layers, in particular those of the p-type, are advantageously deposited from water or other polar solvents on account of their greater solubility in such solvents owing to the presence of a relatively high concentration of positive charges in the polymer backbone. Therefore the water- and/or polar-soluble photocrosslinkers can be advantageously used to fabricate the required multi-layer structures.

Using the crosslinking method here, we fabricated a trilayer polymer organic LED comprising an electron-injecting conducting polymer layer made of crosslinked PEDT:PSSTMA and subsequently surface-modified to become an electron injecting film, an LEP layer made of poly(2-methoxy-5-(3,7-dimethyloctoxy)-p-phenylene vinylene)) ($OC_1C_{10}$-PPV) which is an orange-emitter, a hole-injecting conducting polymer layer made of PEDT:PSSH formulated with a surfactant to allow its deposition on the non-polar and non-wetting LEP layer. Other LEP layers can be used, particularly from the broad classes of polyfluorenes and their copolymers, and polyphenylenevinylenes and their copolymers, as is well known in the state-of-the-art.

This novel device is the prototype of a p-i-n LED structure. One key advantage of such a device structure is the possibility of fabricating a top-emitting display wherein the substrate comprises an opaque silicon or other high-performance semiconductor in which an electrical circuit is embedded. Because the substrate is opaque in contrast to the common situation with bottom-emitting displays, light has to be emitted through the top layer. If the top layer is the cathode layer, then it must be substantially transparent to light but still have a sufficiently low work-function to inject electrons into the device. It is a challenge to deposit the required ultrathin metal cathode films sufficiently thinly (typical required thickness is less than 20 nm) and uniformly over large areas, and that are protected from oxidative degradation. If the top layer is the anode layer, the bottom layer at the substrate level must be the cathode layer. This necessitates the development of cathode films that are substantially stable in air or at least in an inert atmosphere, and that has a sufficiently low workfunction to inject electrons. The metal cathode films in common use do not meet this requirement. It is further advantageous if such layers are made of polymers. The present invention provides an approach for such a transparent low-workfunction polymer layer.

The second key advantage of such a device structure is the possibility of fabricating transparent displays since the p- and n-layers are substantially transparent, compared to the opaque metal cathode layers in current use to fabricate the electron-injecting layer.

The method of fabricating a transparent low-workfunction electron-injecting layer comprises:

(i) Depositing the film conducting polymer formulated with the appropriate amount of photocrosslinker from solution, typically from water- or a polar-solvent, using spin-coating, dip-coating, or printing (including inkjet and offset printing).

(ii) Exposure, with or without photomask patterning, of the layer to render it insoluble, preferably in an inert atmosphere.

(iii) Optionally, replacing the residual acidic H ion in the film by a non-acidic cation, preferably tetramethylammonium ion, preferably by contact ion-exchange with a water-alcohol solution of a salt containing the preferred cation.

(iv) Optionally, fabricating an electrostatic dipole layer on the surface of the film by polyelectrolyte assembly to reduce its workfunction. For this purpose, the polyelectrolyte to be assembled needs to be a polycation, and preferably semiconducting in nature, while the conducting polymer film is preferably a polyanion or substantially polyanion (such as PEDT:PSSH and PEDT:PSSTMA).

(v) Optionally, n-dope the polymer film by contact with a solution of an electron donor, for example, sodium naphthalenide.

(vi) Deposit the LEP layer or other desired subsequent layers.

Fabrication of A P-i-n Trilayer Polymer Organic Light-Emitting Diode

To fabricate the n-layer, 1.6 w/w % PEDT:PSSH (1:2.5 PEDT:PSSH, from Bayer AG) solution in water is mixed with the water-soluble crosslinker N,N-dimethyl-N,N-dipropylene bis(4-azido-2,3,5,6-tetrafluorobenzamide) ammonium triflate to give a ratio of 10 w/w % of the polymer mass. The solution is spun on patterned ITO substrates (cleaned with a mixture of 10:2:0.5 solution of water, hydrogen peroxide and aqueous ammonia, followed by oxygen plasma 150 W, 3 min) to obtain a film with thickness of 50 nm. The film is exposed to deep UV radiation (254 nm, 1 mW cm$^{-2}$, 3 min) in a nitrogen glove box with oxygen and moisture <10 ppm.

The acidic H$^+$ ions are then removed by contact ion-exchange with a 2:1 methanol-water solution of tetramethylammonium (TMA) bromide (Aldrich, 16 mM, 1 min) followed by spin off at 5000 rpm on a spin-coater. The film is then washed twice with 2:1 methanol-water solution on the spinner.

A polyelectrolyte dipole layer is then fabricated over this crosslinked PEDT:PSSTMA film by polyelectrolyte assembly. 0.2 w/w % poly(diallyldimethylammonium chloride) in 2:1 methanol-water mixture was brought into contact with the film for 4 min. Excess solution was spun-off at 4000 rpm. The film was then washed with 2:1 methanol-water three times to remove any unbounded polymer. After this step the workfunction of the PEDT surface as measured by UPS decreases from 5.2 eV (pristine PEDTPSSH) to 3.8 eV, comparable to Al.

The substrates were then transferred to a dry inert environment (glove box) for baking at 120° C. for 5 min.

To deposit the LEP layer, $OC_1C_{10}$-PPV was deposited to obtain a 70-nm thick film from a 3:1 THF: toluene solution.

To deposit the player, a solution of 1.0 w/w % PEDT:PSSH containing 0.055 w/w % of trimethylhexadecylammonium bromide ($Cl_6NMe_3Br$) in a 1:1 water-methanol solution was prepared from commercially-available PEDT:PSSH (1:2.5 PEDT:PSSH, Baytron P from Bayer AG) and $C_{16}NMe_3Br$ (Aldrich). The solution was spin-coated over $OC_1C_{10}$-PPV to give a film thickness of 60 nm. The films were then baked 120° C., 15 min, inside glove box.

The device is finally completed in this case by depositing the anode by evaporating aluminum. For actual applications, the aluminum can be deposited as runners without obscuring the emitting area.

When forward biased (i.e., the negative voltage is applied to the bottom n-layer (i.e., the PEDT:PSSTMA layer), light emission was obtained with a quantum efficiency of 0.01%. When reversed biased, no light emission is obtained. Although the forward biased quantum efficiency is relatively low, this example is given to illustrate the principle that it is possible to obtain electron injection from p-doped conducting polymers provided that it is appropriately surface-modified after crosslinking to give a low workfunction as described here.

Further n-doping of the polymer as described in step (v) decreases the workfunction and improves electron injection efficiency further.

This device structure can also be applied to polymer organic photodiodes, which share a common architecture with polymer organic LEDs, except that the LEP layer is replaced with a charge-generation layer made of material pairs that lead to excited state dissociation and hence charge carrier generation upon illumination by light, as is well known in the state-of-the-art.

B. Low-Workfunction Polymer Electron-Injecting Electrode Film for Polymer Organic Field-Effect Transistor A polymer organic field-effect transistor comprising a pair of source and drain electrodes spanned by a semiconductor layer in contact with a dielectric layer which in turn is in contact with a gate electrode, characterized in that one or both of the source and drain electrodes comprise of a conducting polymer, crosslinked, and preferably n-doped and surface-modified to give the desired low work-function required for electron injection.

The method to fabricate these electrodes follows the outline given in Steps (i)-(v) in the section above.

C. Ion-Sensor

Figure 4:
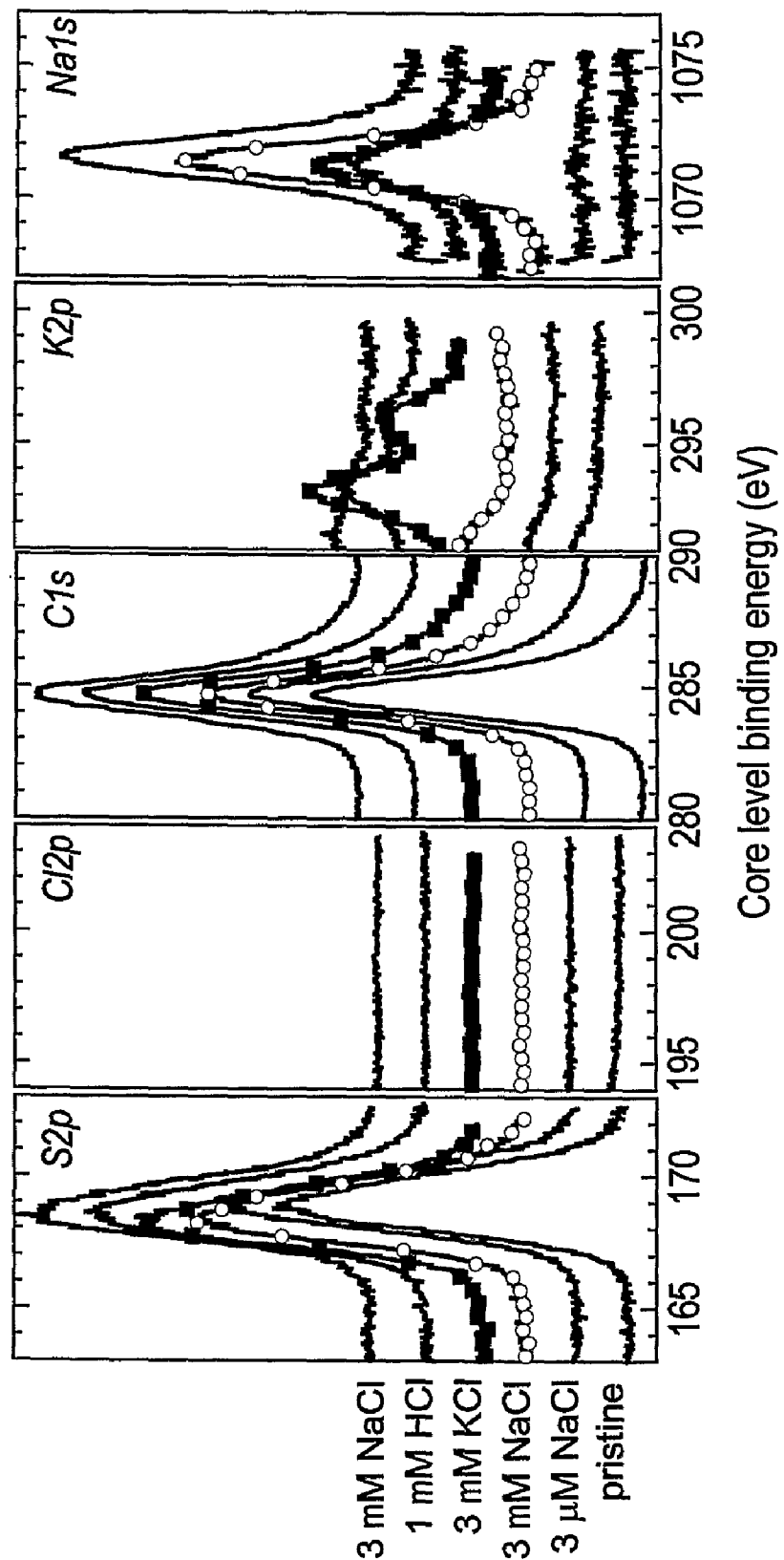
FIG. 4 XPS spectra of a photo-crosslinked 60-nm PSSH film, before and after 10-s contact with 3 μM NaCl, followed by 3 mM NaCl, 3 mM KCl, 1 mM HCl and finally 3 mM NaCl. This experiment reveals the stability of the crosslinked film to $H_2O$ (which would otherwise rapidly dissolve the film) and the reversible ion-exchange enabled. Open circles and closed squares mark a fraction of the NaCl and KCl data for clarity.

To demonstrate a possible application as ion-sensing media, we photo-crosslinked a 60-nm-thick PSSH film on Si and showed that it retains ion-exchange capabilities. Ion-exchange materials are traditionally based on poly(styrenesulfonate) that have been crosslinked by divinylbenzene into beads. These materials obviously cannot be made into thin films. PSSH by itself cannot be used as an ion-exchange membrane because of its water solubility. Here by successfully crosslinking this film, we show it is possible to make sub-100-nm-thick ion-exchange films. X-ray photoelectron spectroscopy (XPS) is used to acquire the elemental core-level spectra of this film (FIG. 4) including the $S_{2p}$, $C_{1s}$, $K_{2p}$, $Cl_{2p}$, $Na_{1s}$ and $N_{1s}$, before and after 10-s exposure to various analyte solutions in the following sequence: 3 µM NaCl, 3 mM NaCl, 3 mM KCl, 1 mM HCl, 3 mM NaCl. No significant exchange occurred after the 10-s contact with the very dilute 3-µM Na$^+$, demonstrating the robustness of the film and the reliability of the XPS measurements. Upon 10-s contact with the 3-mM Na$^+$, complete Na$^+$ exchange in the surface layer occurred, resulting in the appearance of $Na_{1s}$ peak and a shift of the $S_{2p}$ spectrum by −0.5 eV due to ionization (—$SO_2OH$→—$SO_3^-$). Upon 10-s contact with 3-mM $K^+$, half of the $Na^+$ ions were displaced by $K^+$. Upon 10-s contact with 1-mM $H^+$, half of the $K^+$ and also of the remaining $Na^+$ were displaced. Upon the final 10-s contact with 3-mM $Na^+$, both the $H^+$ and $K^+$ ions were fully displaced, while the $Na^+$ intensity returning to full strength. Throughout this experiment, no $Cl^-$ was detected, indicating the changes were purely due to cation exchange in the PSSH film. This experiment confirms that the films are mechanically robust even in contact with water, which strongly swells the film. Secondly, the binding affinity of these three cations vary in the sequence $Na^+>K^+>H^+$, as may be expected on the basis of electrostatic binding. The response can be electrically read, e.g., by impedance spectroscopy, and this therefore forms the basis of a simple chemical/electrochemical sensor. Because different ions swell the film to different extent, this forms also the basis of an ion-actuating film.

EXAMPLES

Synthesis of Crosslinkers

Synthesis of I 3,3'-diamino-N-methyldipropylamine (0.29 mL, 1.79 mmol, Aldrich) and triethylamine (0.55 mL, 3.93 mmol, Aldrich) were dissolved in 40 mL anhydrous $CHCl_3$ and added dropwise to perfluorobenzoyl chloride (0.54 mL, 3.93 mmol, Aldrich) in another 40 ml anhydrous $CHCl_3$. The white precipitate of triethylammonium chloride by-product was filtered off, the filtrate washed with 3×25 mL of half-saturated NaCl solution, then dried with $MgSO_4$, and evaporated to give N-methyl-N,N-dipropylene bis(pentafluorobenzamide) as colorless liquid (yield, 75%). This was then dissolved (777 mg, 1.34 mmol) in 3.2 mL acetone and reacted with 10% excess sodium azide (192 mg, 2.95 mmol) dissolved in 1.5 mL water and 3 mL acetone, under reflux for 5-8 hours. Excess acetone was added, the white precipitate of NaF was filtered off, and the yellow filtrate washed with 3×25 mL of half saturated NaCl solution, dried with $MgSO_4$, and evaporated to give N-methyl-N,N-dipropylene bis(4-azido-2,3,5,6-tetrafluorobenzamide) as a pale yellow solid (yield, 65%). This was then dissolved (505 mg, 0.87 mmol) in 10 mL anhydrous $CHCl_3$, and reacted with excess iodomethane (5 mL, 80.3 mmol) overnight at room temperature. The fine pale yellow precipitate was filtered off and recrystallized twice in water to give N,N-dimethyl-N,N-dipropylene bis(4-azido-2,3,5,6-tetrafluorobenzamide) ammonium iodide (I) as pale yellow crystals (yield, 55%). $^1H$ NMR (ppm, MeOD)= 4.56 (s), 3.50 (t, J=6.6 Hz, 2H), 3.42 (m, 2H), 3.15 (s, 3H), 2.12 (m, 2H). $^{19}F$ NMR (ppm, MeOD)=−68.35 (d, J=25 Hz), −76.97 (d, J=24 Hz). FTIR ($cm^{-1}$)=3300 (NH), 3078 (NH), 3032 (NH), 2968 ($CH_3$), 2942 ($CH_2$), 2885 ($CH_2$), 2157-2129 ($N_3$), 1658 (CO), 1549 (CONH), 1486 ($N_3$), 1437 ($CH_2$), 1407 ($CH_3$, $CH_2$), 1338 ($N_3$), 1278 ($N_3$), 1024, 1000, 989.

The material is soluble in methanol, methanol-rich water mixtures, and other lower alcohols.

The iodide anion can be ion-exchanged to other ions, for example, perchlorate, hexafluorophosphate, p-toluenesulfonate, tetrafluoroborate and triflate to impart the appropriate solubility in the chosen solvent, and for appropriate thermal stability.

Synthesis of II-V:

The iodide anion in I is exchanged by reacting with the appropriate stoichiometric amount of Ag(I) salt of $PF_6^-$ (to give II), $BF_4^-$ (to give III), $ClO_4^-$ (to give VI) and $CF_3COO^-$ (to give V) in MeOH. The AgI by-product was filtered off, and the filtrate evaporated under reduced pressure to recover the various anion-exchanged member. Their identities were confirmed through the anion-specific vibrational modes (see Table 1). The vibrations of the N,N-dimethyl-N,N-dipropylene bis(4-azido-2,3,5,6-tetrafluorobenzamide) ammonium backbone remain essentially unchanged. FTIR analysis indicates that II, III and IV were obtained in the anhydrous form, whereas I and V contained significant water of crystallization. All ion-exchange reactions were conducted in the dark light to prevent photoinduced Ag(I) reduction.

TABLE 1

Physical properties of crosslinkers. Melting point was determined on a calibrated melting point apparatus (10° C. $min^{-1}$). Anion infrared frequencies were measured in KBr.

| | X− | Appearance | mp(° C.) | Anion infrared frequencies ($cm^{-1}$) |
|---|---|---|---|---|
| I | $I^-$ | Light yellow cubic crystals | 133-136 | — |
| II | $PF_6^-$ | Off-white cubic crystals | 134-140 | $v_{PF}$ = 882, 870, 836 |
| III | $BF_4^-$ | White needle-like crystals | 145-147 | $v_{BF}$ = 1123, 1083, 1058 |
| IV | $ClO_4^-$ | Off-white cubic crystals | 142-145 | $v_{ClO}$ = 1150, 1120, 1090 |
| V | $CF_3COO^-$ | Low-melting crystals | — | $v_{CF}$ = 1208, 1130 |

This series was synthesized from the parent I by anion-exchange in MeOH of the $I^-$ in I with other anions from the appropriate Ag(I) salts. I was synthesized by amide coupling of the carboxy perfluoro rings to the bridge, followed by nucleophilic aromatic $N_3$ substitution, and methylation-quartenization of the imine group in the bridge. The identity of the final product is confirmed through FTIR spectroscopy of the anion-specific vibrations. The backbone vibrations of I including its azide group are unaffected (see Examples). The anion controls the solubility characteristics and physical properties. Therefore while I to V are readily soluble in the lower alcohols (including methanol (MeOH), ethanol (EtOH) and iso-propanol (i-PrOH)), acetone and polar aprotic solvents (including dimethylsulfoxide (DMSO), N,N-dimethylformamide (DMF), N,N-dimethylacetamide (DMAc) and N-methylpyrrolidone (NMP)), and have melting temperatures in the 135-145° C. range, V is also soluble in $H_2O$ with a considerably lower melting temperature. It is possible to formulate these compounds into polyelectrolyte films using the appropriate solvents. In particular, FTIR analysis indicates that II, III and IV do not contain water of crystallization (as evidenced by the absence of the $H_2O$ absorption band at 3000-4000 $cm^{-1}$), and are therefore suitable also in anhydrous applications.

Radiation Crosslinking

Silicon (Si) wafers were diced into 10×10 mm squares and treated with 3-aminopropyltrimethoxysilane (APS, Aldrich) for good adhesion of the polyelectrolyte to the substrate. In a typical procedure, Si wafers were pre-cleaned with acetone, isopropanol and oxygen plasma (250 W, 5 min) were treated with 2.5 mM APS solution in hexane at reflux for 3 h under nitrogen. The wafers were then cleaned in 3 rounds of hexane, and then baked at 120° C. for 10 min.

To assess the crosslinking efficiency, polymer solutions were formulated with the selected crosslinker and spin-cast onto clean pristine Si wafers or the APS-treated Si wafers to give 50-200-nm thick films. The films were then transferred to a nitrogen glovebox and dehydrated before exposure to 254-nm DUV from a low-pressure Hg lamp (1 mW cm$^{-2}$) also in the glovebox. The photoexposed films were then baked at 150° C. for 1-2 min to improve adhesion to the substrates, and developed with the appropriate solvent (usually $H_2O$, MeOH or i-PrOH-$H_2O$ mixture).

It is to be understood that while the invention has been described in conjunction with the detailed description thereof, that the foregoing description is intended to illustrate and not limit the scope of the invention in any way.

The invention claimed is:

1. A crosslinking compound of formula (1):

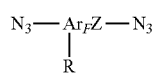
(1)

wherein $Ar_FZ$ comprises one or more fluorinated aromatic group;

and R comprises one or more ionisable group, wherein the one or more ionisable group is selected from the group consisting of an acid group selected from the group consisting of a sulfonic acid, a phosphonic acid, a carboxylic acid, a cationic group selected from the group consisting of a quaternary ammonium group and a pyridinium group, a basic group selected from the group consisting of amine, and an anionic group selected from the group consisting of a sulfonate, a phosphonate and a carboxylate, wherein the crosslinking compound is soluble in at least one polar solvent selected from the group consisting of water, methanol, ethanol, propanol, dimethylsulfoxide, N,N-dimethylformamide, N,N-dimethylacetamide, N-methylpyrrolidone.

2. The crosslinking compound of claim 1 wherein the one or more fluorinated aromatic group comprises two fluorinated aromatics.

3. The crosslinking compound of claim 2 further comprising a linker connecting the two fluorinated aromatics.

4. The crosslinking compound of claim 1 wherein each of the one or more fluorinated aromatic group are independently selected from the group consisting of fluorinated phenyl and fluorinated napthyl.

5. The crosslinking compound of claim 4, wherein each of the one or more fluorinated aromatic group bears fluorine atoms ortho in position to an azide group.

6. The crosslinking compound of claim 2 wherein the two fluorinated aromatics are fluorinated phenyl.

7. The crosslinking compound of claim 3 wherein the linker is joined to each of the two fluorinated aromatics by an electron-withdrawing group.

8. The crosslinking compound of claim 7 wherein the electron-withdrawing group is selected from the group consisting of a carbonyl, an ester and an amide.

9. The crosslinking compound of claim 3 wherein the linker is selected from the group consisting of a $C_1$ to $C_8$ alkylene, cyclohexylene and alkylidene.

10. The crosslinking compound of claim 3 wherein the ionisable group is bonded to the linker.

11. The crosslinking compound of claim 1 wherein an absorption band occurs above between 250 nm to 450 nm.

12. A crosslinking compound according to formula (2):

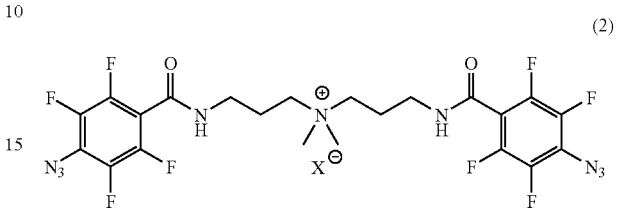
(2)

wherein X is selected from the group consisting of I, $PF_6$, $BF_4$, $ClO_4$ and $CF_3COO$.

13. A mixture comprising a polymer and the crosslinking compound according to claim 1, wherein the concentration of the crosslinking compound is in the range of 0.1% to 20% w/w of the polymer.

14. The mixture of claim 13 wherein the concentration of the crosslinking compound is in the range of 0.1% to 5.0%.

15. The mixture of claim 13 wherein the polymer is selected from the group consisting of polymer soluble in one or more polar solvents.

16. The mixture of claim 15 wherein the polar solvent is selected from the group of consisting of water, methanol, ethanol, propanol, dimethylsulfoxide, N,N-dimethylformamide, N,N-dimethylacetamide, N-methylpyrrolidone.

17. The mixture of claim 15 wherein the polymer is selected from the group consisting of poly(styrene sulfonic acid), poly(styrene sulfonate salt), poly(diallydimethylammonium salt), poly(ally amine), poly(3,4-ethylenedioxythiophene)-poly(styrene sulfonic acid), poly(3,4-ethylenedioxythiophene)-poly(styrene sulfonate salt).

18. A method of crosslinking a polymer, the method including the steps of:
(i) adding the crosslinking compound of claim 1 to a polymer selected from the group consisting of poly(styrene sulfonic acid), poly(styrene sulfonate salt), poly(diallydimethylammonium salt), poly(ally amine), poly(3,4-ethylenedioxythiophene)-poly(styrene sulfonic acid), poly(3,4-ethylenedioxythiophene)-poly(styrene sulfonate salt) in a compatible solvent to give a solution; and
(ii) depositing a film from the solution on a substrate; and
(iii) soft-baking the film at a temperature between 100° C. and 130° C.; and
(iv) photocrosslinking the film to form an insoluble crosslinked polymer.

* * * * *